United States Patent
O'Brien et al.

(10) Patent No.: US 8,317,729 B2
(45) Date of Patent: Nov. 27, 2012

(54) CERVICAL DILATION METER

(75) Inventors: John M. O'Brien, Lexington, KY (US); Dirk V. Hoyns, Jackson, GA (US)

(73) Assignee: Glenveigh Medical, LLC, Chatanooga, TN (US)

( * ) Notice: Subject to any disclaimer, the term of this patent is extended or adjusted under 35 U.S.C. 154(b) by 522 days.

(21) Appl. No.: 12/543,391

(22) Filed: Aug. 18, 2009

(65) Prior Publication Data
US 2010/0049094 A1 Feb. 25, 2010

Related U.S. Application Data

(60) Provisional application No. 61/089,763, filed on Aug. 18, 2008.

(51) Int. Cl.
*A61B 5/103* (2006.01)
*A61B 5/117* (2006.01)
(52) U.S. Cl. .......... 600/591; 600/587; 600/588
(58) Field of Classification Search .......... 600/591, 600/588, 587, 551, 300, 304
See application file for complete search history.

(56) References Cited

U.S. PATENT DOCUMENTS

| | | | |
|---|---|---|---|
| 1,193,988 A * | 8/1916 | Burdin | 606/135 |
| 1,664,112 A * | 3/1928 | Junemann | 606/158 |
| 2,217,968 A * | 10/1940 | Radcliff | 606/198 |
| 2,579,849 A * | 12/1951 | Newman | 600/215 |
| 2,924,220 A | 2/1960 | Von Micsky | |
| 3,182,662 A * | 5/1965 | Shirodkar | 606/119 |
| 3,768,459 A | 10/1973 | Cannon et al. | |
| 3,937,212 A | 2/1976 | Fletcher et al. | |
| 4,141,345 A | 2/1979 | Allen et al. | |
| 4,207,902 A | 6/1980 | Krementsov | |
| 4,245,656 A | 1/1981 | Farr et al. | |

(Continued)

FOREIGN PATENT DOCUMENTS

GB 1573911 8/1980

(Continued)

OTHER PUBLICATIONS

Lucidi, R., et al., "Cervimetry: A Review of Methods for Measuring Cervical Dilation During Labor", *Obstetrical & Gynecological Survey*, 55(5), [online]. (c)2000-2007 Ovid Technologies, Inc. [retrieved Jul. 10, 2008]. Retrieved from the Internet: <URL: http://libproxy.main.erlanger.org:3156/spb/ovidweb.cgi>, 13 pgs.

(Continued)

*Primary Examiner* — Jeffrey G Hoekstra
(74) *Attorney, Agent, or Firm* — Schwegman Lundberg Woessner P.A.

(57) ABSTRACT

An instrument for measuring cervical dilation can have a pair of arms connected at their proximal ends to an arm pivot or articulating member, the arms being in movable communication with a gauge assembly for measuring the relative distance between the arms at a fixed location near the proximal ends of the arms. The arms can be disposed to apply an outward lateral pressure against the walls of the cervix, thereby engaging the cervix without the need for physical penetration, gripping, or other attachment of the device to the cervical tissue. Continuous outward lateral pressure of the arms against the cervical walls can allow the arms to expand in response to and in concert with expansion and dilation of the cervix. The relative distance between the arms correlates to the diameter of the cervix, such that the correlated measurement indicated on a scale of the gauge means is the measurement of cervical dilation.

27 Claims, 13 Drawing Sheets

U.S. PATENT DOCUMENTS

| | | | |
|---|---|---|---|
| 4,362,167 A | | 12/1982 | Nicolai et al. |
| 4,476,871 A | | 10/1984 | Hon |
| 4,502,485 A | * | 3/1985 | Burgin .......................... 606/191 |
| 4,611,603 A | | 9/1986 | Kelso et al. |
| 4,682,609 A | | 7/1987 | Parsons |
| 4,719,925 A | | 1/1988 | Parsons |
| 5,222,485 A | | 6/1993 | Jerath |
| 5,450,857 A | | 9/1995 | Garfield et al. |
| 5,578,043 A | * | 11/1996 | Galstian .......................... 606/119 |
| 5,658,295 A | | 8/1997 | Krementsov |
| 5,713,371 A | | 2/1998 | Sherman et al. |
| 5,807,281 A | | 9/1998 | Welch |
| 5,829,438 A | | 11/1998 | Gibbs et al. |
| 5,851,188 A | | 12/1998 | Bullard et al. |
| 5,876,357 A | | 3/1999 | Tomer |
| 5,935,061 A | | 8/1999 | Acker et al. |
| 6,039,701 A | | 3/2000 | Sliwa et al. |
| 6,066,104 A | | 5/2000 | Dao et al. |
| 6,200,279 B1 | | 3/2001 | Paltieli |
| 6,270,458 B1 | | 8/2001 | Barnea |
| 6,383,137 B1 | | 5/2002 | Berry |
| 6,419,646 B1 | | 7/2002 | Baxter-Jones |
| 6,423,000 B1 | | 7/2002 | Berry |
| 6,423,016 B1 | | 7/2002 | Hamilton et al. |
| 6,450,977 B1 | | 9/2002 | Baxter-Jones |
| 6,524,259 B2 | | 2/2003 | Baxter-Jones et al. |
| 6,540,977 B1 | | 4/2003 | van de Winkel |
| 6,669,653 B2 | | 12/2003 | Paltieli |
| 6,802,817 B2 | | 10/2004 | Baxter-Jones et al. |
| 6,802,917 B1 | | 10/2004 | Tomantschger et al. |
| 6,905,472 B2 | | 6/2005 | Welch |
| 6,966,881 B2 | | 11/2005 | Ben-Cnaan et al. |
| 6,994,678 B2 | | 2/2006 | Baxter-Jones et al. |
| 7,052,457 B2 | * | 5/2006 | Fanous .......................... 600/220 |
| 7,150,108 B2 | | 12/2006 | Babb |
| 7,153,280 B2 | | 12/2006 | Welch |
| 7,207,941 B2 | | 4/2007 | Sharf |
| 7,549,997 B2 | | 6/2009 | Davis, Jr. |
| 2003/0158502 A1 | | 8/2003 | Baxter-Jones et al. |
| 2004/0059193 A1 | * | 3/2004 | Fanous .......................... 600/220 |
| 2004/0122463 A1 | | 6/2004 | Hibler |
| 2004/0225196 A1 | * | 11/2004 | Ruane .......................... 600/220 |
| 2004/0225235 A1 | | 11/2004 | Ben-Cnaan et al. |
| 2005/0049509 A1 | | 3/2005 | Mansour et al. |
| 2005/0267509 A1 | | 12/2005 | Davis, Jr. |
| 2006/0020230 A1 | | 1/2006 | Baxter-Jones et al. |
| 2007/0156067 A1 | | 7/2007 | Dubey et al. |
| 2007/0156068 A1 | | 7/2007 | Dubey et al. |
| 2007/0179410 A1 | | 8/2007 | Mahajan et al. |
| 2007/0213640 A1 | | 9/2007 | Mansour et al. |
| 2007/0239197 A1 | | 10/2007 | Dubey et al. |
| 2007/0255185 A1 | | 11/2007 | Dubey et al. |
| 2008/0021350 A1 | | 1/2008 | Bechtle et al. |
| 2008/0033322 A1 | | 2/2008 | Feuer et al. |
| 2008/0114268 A1 | | 5/2008 | Dubey et al. |

FOREIGN PATENT DOCUMENTS

| | | |
|---|---|---|
| WO | WO-8703189 | 6/1987 |
| WO | WO-8703189 A1 | 6/1987 |
| WO | WO-9809565 | 3/1998 |
| WO | WO-9809565 A1 | 3/1998 |
| WO | WO-9907300 | 2/1999 |
| WO | WO-9907300 A1 | 2/1999 |
| WO | WO-9926537 | 6/1999 |
| WO | WO-9926537 A1 | 6/1999 |
| WO | WO-0051494 | 9/2000 |
| WO | WO-0051494 A1 | 9/2000 |
| WO | WO-0176477 | 10/2001 |
| WO | WO-0176477 A1 | 10/2001 |
| WO | WO-2004041059 | 5/2004 |
| WO | WO-2004041059 A2 | 5/2004 |
| WO | WO-2004098375 | 11/2004 |
| WO | WO-2004098375 A2 | 11/2004 |
| WO | WO-2007078449 | 7/2007 |
| WO | WO-2007078449 A1 | 7/2007 |
| WO | WO-2008016812 | 2/2008 |
| WO | WO-2008016812 A2 | 2/2008 |
| WO | WO-2010/021689 A1 | 2/2010 |

OTHER PUBLICATIONS

Sharf, Y., et al., "Continuous Monitoring of Cervical Dilatation and Fetal Head Station During Labor", *Medical Engineering & Physics*, 29, (2007), 61-71.

"International Application Serial No. PCT/US2009/004700, Search Report mailed Mar. 3, 2009".

"International Application Serial No. PCT/US2009/004700, Written Opinion mailed Nov. 3, 2009".

Lucidi, R. S., et al., "Cervimetry: a review of methods for measuring cervical dilatation during labor", *Obstetrical & Gynecological Survey*, 55(5), (May 2000), 312-20.

Sharf, Y., et al., "Continuous monitoring of cervical dilatation and fetal head station during labor", *Medical Engineering & Physics*, 29(1), (Jan. 2007), 61-71.

"Chinese Application Serial No. 200980141407.3, Voluntary Amendment filed Apr. 12, 2012", English Translation Only, 7 pgs.

"European Application Serial No. 09789157.6, Office Action mailed Feb. 8, 2012", 6 pgs.

\* cited by examiner

CERVICAL DILATION METER

CLAIM OF PRIORITY

This patent application claims the benefit of priority of U.S. Provisional Patent Application Ser. No. 61/089,763, entitled CERVICAL DILATION METER, filed on Aug. 18, 2008, which is hereby incorporated by reference herein in its entirety.

BACKGROUND

The cervix is the portion of the uterus connecting the uterus to the vagina. The cervix is cylindrical or conical in shape, approximately one inch in length, and having a cervical canal passing through it with an external os opening to the vaginal cavity and internal os opening to the uterine cavity. During labor and delivery, the cervical canal is the channel through which the baby passes from the uterine cavity into the vaginal cavity. During labor, the position (station) of the cervix rotates from posterior to anterior During labor, in response to coordinated uterine contractions and pressure created by the descending fetal head, the length of the cervix shortens and the cervical walls thin in a process known as "effacement", and the cervix opens further or dilates. Effacement can be quantified in percentage, from 0% (no change) to 100% (completely thinned). Cervical dilation can be quantified as the diameter of the cervical opening, e.g., in centimeters ranging from zero (0) to ten (10) centimeters. When the cervix dilates to ten (10) centimeters or greater, the cervical dilation can be deemed complete, and the patient can be encouraged to push the baby out. Before effacement and complete dilation, patients are encouraged not to push due to the risk of injury to both mother and baby. Effacement and dilation are critical indicators of the progress, or lack of progress, of labor. The degree and rate of effacement and dilation are monitored periodically during the first stage of labor. Slow or inadequate cervical dilation may indicate the need for administering a cervical ripening drug or applying a cervical dilating instruments or the need for surgical delivery.

A digital palpation is currently the standard procedure clinicians (physician, nurse, mid-wife, etc.) use to measure the cervical diameter. In digital examination, the clinician inserts a gloved hand into the vagina and uses the middle and index fingers to palpate or probe the cervix and external cervical os. The fingertips palpate and locate the external cervical os and are then spread until the fingertips contact opposing walls of the cervix. The distance between the spread fingertips corresponds to the cervical diameter. Using the digital palpation approach, the degree of dilation of the cervical os is estimated without any means to confirm visually the spacing between the index and middle fingers while situated within the cervical os.

During the course of labor in a patient, one or more clinicians perform, on average, ten digital examinations. However, digital examination provides only intermittent data for assessment of labor progression. Furthermore, the accuracy of digital examination is very subjective and may depend upon many factors, including the experience, judgment, and the size of the clinician's fingers, and error caused by the stretching of the cervix by the clinician's fingers. Although an individual clinician may achieve acceptable repeatability and accuracy using this method, it is normal to see a one (1) centimeter error or variation in measurement among serial measurements by the same clinician. If different clinicians examine the same patient during the course of labor, the inaccuracy of cervical dilation measurements increases due to inter-clinician variability.

Inaccurate or inconsistent measurements of cervical dilation may hinder the early detection of dysfunctional labor or delivery complications. Furthermore, despite the use of gloves, digital examination increases the risk of infection of the fetal membranes (chorioamnionitis), the lining and/or muscle of the uterus (endomyometritis), or of the infant (neonatal sepsis). This risk increases significantly after the fetal membranes have ruptured, and the risk of infection correlates to the number of digital exams. For this reason, it is preferable to minimize the number of digital exams, particularly after the fetal membranes have ruptured. Other disadvantages of digital examination measurements to determine cervical dilation include the inability to monitor dilation continuously, the procedure may dislodge fetal or uterine monitors, and the procedure is embarrassing and causes even more discomfort to the mother who is already experiencing significant pain due to labor.

Various mechanical and electrical systems have been devised to measure cervical dilation. See, e.g., *Cervimetry: A Review of Methods for Measuring Cervical Dilation During Labor*, Obstetrics & Gynecology Survey, Vol. 55(5): 312-320 (2000); see also, e.g., Sharf Y, Farine D. et al., *Continuous Monitoring of Cervical Dilation and Fetal Head Station During Labor*, Medical Engineering & Physics 29: 61-71 (2007). See also, e.g., the following U.S. patent Nos. and U.S. patent application Publication Nos.: U.S. Pat. Nos. 2,924,220; 3,768,459; 4,141,345; 4,207,902; 4,245,656; 4,476,871; 4,611,603; 4,682,609; 4,719,925; 5,222,485; 5,450,857; 5,658,295; 5,713,371; 5,935,061; 6,039,701; 6,066,104; 6,200,279; 6,270,458; 6,383,137; 6,419,646; 6,423,000; 6,423,016; 6,524,259; 6,540,977; 6,669,653; 6,802,917; 6,966,881; 6,994,678; 7,150,108; 7,207,941; US 2005/0049509; US 2006/0020230; US 2007/0156067; US 2007/0156068; US 2007/0179410; US 2007/0179410; US 2007/0213640; US 2008/0021350; and also PCT Patent Application Publications WO 1987/03189; WO 2000/051494; WO 2004/098375; WO 2004/00373.

SUMMARY/OVERVIEW

The present inventors have recognized, among other things, that, unfortunately, none of the above-mentioned methods or devices have gained commercial acceptance for many reasons, including: patient discomfort and cervical tissue trauma due to attachment, penetration or active fixation engagement of the device to the cervical tissue (e.g., by needles, barbs, hooks, clamps, grips, or sutures); lack of accuracy due to cervical tissue distortion; inability to isolate measurement of cervical os dilation from measurement of changes in the station or movement of cervix during the progression of labor; blockage of the cervical canal (thus inhibiting descent of the fetal head and monitoring of fetal status and labor progression by known monitoring devices); complexity of the device or its installation; lack of disposability (thus high cost or a need to sterilize the device for later reuse in the patient); radiation, ultrasonic and electrical shock hazards; and unsuitability for patient ambulation or home use. Consequently, the present inventors have recognized and believe that there is currently no commercially available simple, objective mechanical monitoring device or system to measure cervical diameter, and digital examination continues to be the preferred method for measuring cervical diameter and dilation.

Thus, the present inventors have recognized, among other things, the usefulness of an objective monitoring device that can accurately measure cervical dilation, that can measure cervical dilation in different cervical stations and during changes in cervical station, that need not be invasive (need not penetrate tissue by barbs, needles, clips, sutures, or other invasive means) and need not grip, clamp or compress the cervix or otherwise distort the cervix. The present inventors have also recognized the usefulness of a device to monitor cervical dilation that can be placed and retained in the patient throughout the first stage of labor, thereby allowing continuous or ongoing monitoring of cervical dilation. The present inventors have also recognized the usefulness of a device for measuring cervical dilation that can remain in place in the patient without obstructing descent of the fetal head (which can inhibit delivery) and that can easily be displaced or expelled from the patient, such as by the natural progression of labor, without requiring manual removal by the clinician. The present inventors have also recognized the usefulness of a device that has a measurement scale that can be located outside the body and that can be simple enough to interpret that the patient or her family can directly monitor the patient's cervical dilation, without the need for clinician oversight. The present inventors have also recognized the usefulness of a cervical dilation monitoring device that can permit the patient to remain ambulatory while the device is in place. In certain examples, the present devices and methods can provide one or more of such useful characteristics in monitoring cervical dilation. To better illustrate the subject matter described herein, a non-limiting list of examples follows.

Example 1 describes an apparatus comprising first and second arms, comprising respective proximal and distal portions, the proximal portions of the first and second arms coupled together, the distal portions of the first and second arms configured to be inserted between, and to exert enough of an outward force against, opposing lateral walls of a cervix or vagina to hold the apparatus in position, while measuring cervical dilation, without requiring active fixation to the cervix or vagina. In this example, a cervical dilation gauge assembly, communicatively coupled to the first and second arms to receive information about the cervical dilation, and comprising an external cervical dilation indicator to provide an indication of the cervical dilation to a user.

In Example 2, the apparatus of Example 1 is optionally configured such that an intermediate region of the first arm comprises an outwardly bowed first cephalic curve, and wherein an intermediate region of the second arm comprises an outwardly bowed second cephalic curve, and wherein concave portions of the first and second cephalic curves are opposing each other.

In Example 3, the apparatus of any one or any combination of Examples 1-2 is optionally configured such that the concave portions of the first and second cephalic curves are sized and shaped to receive and accommodate a fetal head therebetween.

In Example 4, the apparatus of any one or any combination of Examples 1-3 is optionally configured such that the concave portions of the first and second cephalic curves are sized and shaped to receive a descending fetal head therebetween during birthing while the first and second arms continue to exert enough of an outward force against opposing lateral walls of a cervix or vagina to hold the apparatus in position while measuring cervical dilation without requiring active fixation to the cervix or vagina.

In Example 5, the apparatus of any one or any combination of Examples 1-4 is optionally configured such that the first and second arms comprise respective first and second pelvic curves at or near a location between the intermediate and proximal portions of the respective first and second arms, such that the respective intermediate portions of the respective first and second arms angle or curve upward from the respective proximal portions of the respective first and second arms at an angle that is about 15 degrees to allow placement of the apparatus if the cervix is in a mid or anterior position.

In Example 6, the apparatus of any one or any combination of Examples 1-5 optionally comprises a spring, providing a force that is coupled to the first and second arms to bias the first and second arms away from each other.

In Example 7, the apparatus of any one or any combination of Examples 1-6 is optionally configured such that the spring is configured to exert enough of an outward force of the first and second arms against opposing lateral walls of the cervix or vagina to hold the apparatus in position while measuring cervical dilation without requiring active fixation to the cervix or vagina, and without exerting so much outward force so as to substantially affect the measuring of the cervical dilation.

In Example 8, the apparatus of any one or any combination of Examples 1-7 is optionally configured such that distal portions of the respective first and second arms respectively comprise first and second feet that are respectively coupled to respective intermediate portions of the respective first and second arms by respective first and second flexible members that are respectively more flexible than the respective first and second feet and the respective intermediate portions of the respective first and second arms, and wherein the respective first and second feet flex at respective angles, with respect to the respective first and second arms, in a plane formed by intermediate portions of the first and second arms.

In Example 9, the apparatus of any one or any combination of Examples 1-8 is optionally configured such that the first and second feet are respectively angled upward from a plane formed by the respective intermediate portions of the first and second arms by an angle that is about 30 degrees.

In Example 10, the apparatus of any one or any combination of Examples 1-9 is optionally configured such that the first and second feet respectively provide a surface area of at least about 2.0 cm$^2$ for contacting the cervix.

In Example 11, the apparatus of any one or any combination of Examples 1-10 optionally comprises a rotational pivot joint, coupling the proximal portions of the first and second arms together; and a spring, coupled to the first and second arms to exert an outward force to drive the first and second arms apart.

In Example 12, the apparatus of any one or any combination of Examples 1-11 optionally is configured such that the spring is located at a proximal end of a member extending from a location near or distal to the rotational pivot joint to a more proximal external location.

In Example 13, the apparatus of any one or any combination of Examples 1-12 is optionally configured such that the spring is located at the external location.

In Example 14, the apparatus of any one or any combination of Examples 1-13 is optionally configured such that the member comprises a cable.

In Example 15, the apparatus of any one or any combination of Examples 1-14 is optionally configured such that the member comprises a portion of a rack-and-pinion assembly.

In Example 16, the apparatus of any one or any combination of Examples 1-15 is optionally configured such that the spring is located at the rotational pivot joint.

In Example 17, the apparatus of any one or any combination of Examples 1-16 optionally comprises a stem including: a proximal portion coupled to the external indicator of cervical dilation; and a distal portion coupled to the proximal portion of at least one of the first and second arms.

In Example 18, the apparatus of any one or any combination of Examples 1-17 optionally comprises an introducer sheath, sized and shaped to constrain the first and second arms toward each other during insertion of the apparatus, and to permit removal of the sheath over the stem.

In Example 19, the apparatus of any one or any combination of Examples 1-18 optionally comprises a cable including a proximal portion coupled to the external indicator of cervical dilation, and a distal portion coupled to at least one of the first and second arms, and wherein the cable is constrained such that a position of a proximal end of the cable is correlative to the cervical dilation.

In Example 20, the apparatus of any one or any combination of Examples 1-19 optionally comprises a spring, coupled to a proximal end of the cable, the spring configured to tend to move the proximal end of the cable in a proximal direction to exert, via the cable, a force on at least one of the first and second arms to tend to move respective portions of the first and second arms apart.

Example 21 describes a method comprising: inserting first and second arms of a cervical dilation measuring apparatus into a vagina such that respective distal portions of the first and second arms exert enough of an outward force against, opposing lateral walls of a cervix or vagina to hold the apparatus in position, while measuring cervical dilation, without requiring active fixation to the cervix or vagina; communicating information about the cervical dilation to an external location; and providing an external indicator of the cervical dilation to a user, using the information.

In Example 22, the method of Example 21 optionally comprises inserting first and second arms comprising respective outwardly bowed cephalic curves, wherein concave portions of the respective cephalic curves oppose each other.

In Example 23, the method of any one or any combination of Examples 21-22 optionally comprises comprising receiving a fetal head between portions of the first and second arms.

In Example 24, the method of any one or any combination of Examples 21-23 optionally comprises receiving a fetal head between portions of the first and second arms during birthing while the first and second arms continue to exert enough of an outward force against opposing lateral walls of a cervix or vagina to hold the apparatus in position while measuring cervical dilation without requiring active fixation to the cervix or vagina.

In Example 25, the method of any one or any combination of Examples 21-24 optionally comprises placing the apparatus when the cervix is in a mid or anterior position such that respective intermediate portions of the respective first and second arms angle or curve upward from respective proximal portions of the respective first and second arms at an angle that is about 15 degrees.

In Example 26, the method of any one or any combination of Examples 21-25 optionally comprises exerting enough of an outward force of the first and second arms against opposing lateral walls of the cervix or vagina to hold the apparatus in position while measuring cervical dilation without requiring active fixation to the cervix or vagina, and without exerting so much outward force so as to substantially affect the measuring of the cervical dilation.

In Example 27, the method of any one or any combination of Examples 21-26 optionally comprises inserting into a cervical os first and second feet at respective distal portions of the first and second arms, such that the first and second feet flex at an angle, with respect to the respective first and second arms, in a plane formed by intermediate portions of the first and second arms.

In Example 28, the method of any one or any combination of Examples 21-27 optionally comprises inserting into the cervical os the substantially flat first and second feet at respective distal portions of the first and second arms, such that the first and second feet are angled upward with respect to the plane formed by the intermediate portions of the first and second arms.

In Example 29, the method of any one or any combination of Examples 21-28 optionally is performed such that communicating information about a cervical dilation to an external location comprises receiving the information using a longitudinal position translation correlative to a degree of pivoting of intercoupled proximal portions of the first and second arms.

In Example 30, the method of any one or any combination of Examples 21-29 optionally is performed such that using a longitudinal position translation correlative to a degree of pivoting of intercoupled proximal portions of the first and second arms comprises using at least one of: a position of a rack in a rack-and-pinion; or a position of a proximal end of a member, wherein the member is constrained such that the proximal end of the member represents the degree of pivoting.

This overview is intended to provide an overview of the subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
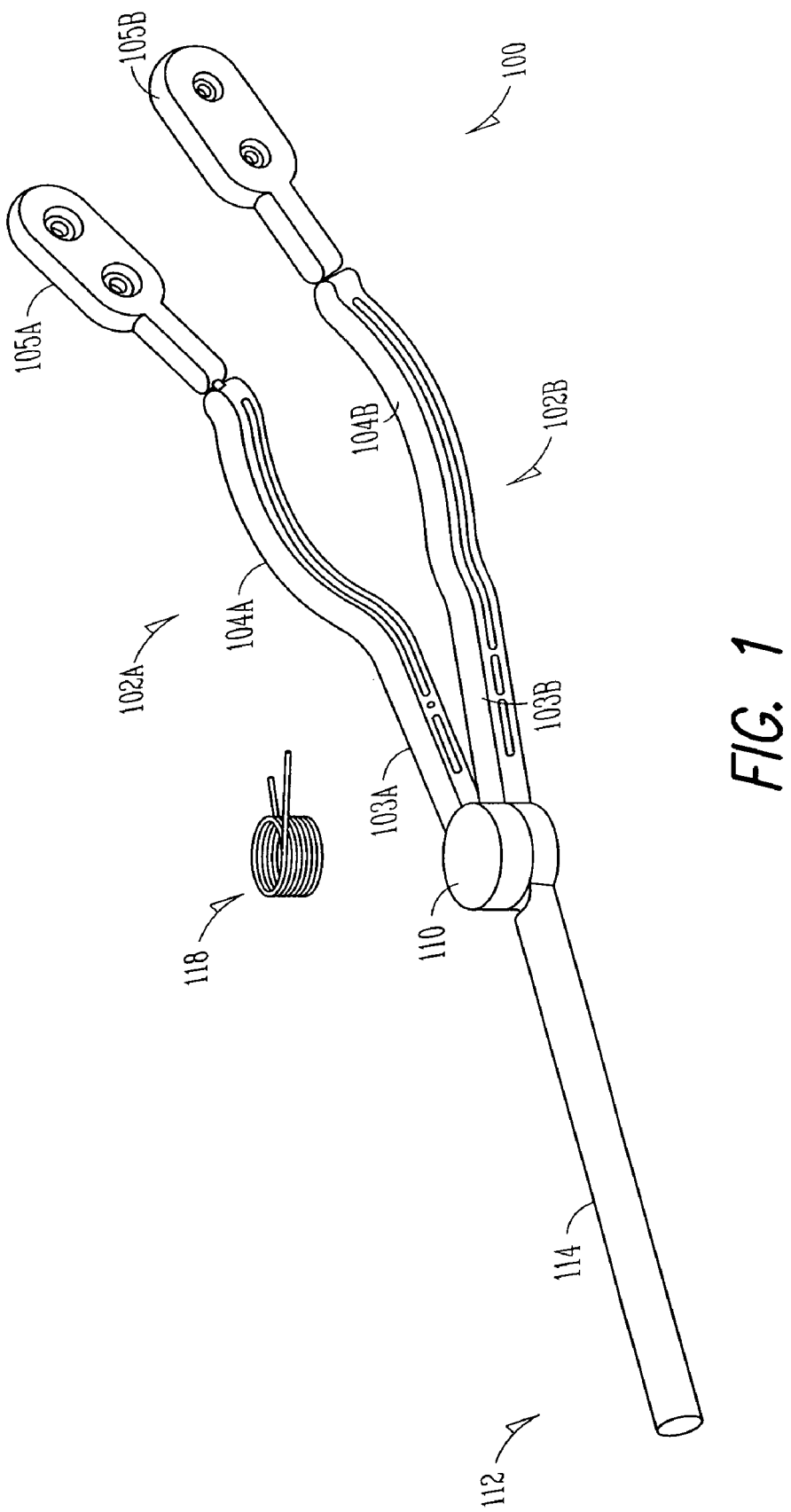
FIG. 1 illustrates an isometric drawing of an example of portions of a cervical dilation meter apparatus.

FIG. 1 illustrates an isometric drawing of an example of portions of a cervical dilation meter 100 apparatus. In this example, the cervical dilation meter 100 can include arms 102A-B, which can be drawn together into a closed position, such as for insertion. In an example, the arms 102A-B can include respective proximal portions 103A-B, intermediate portions 104A-B, and distal portions 105A-B, which can be configured such as shown in the example of FIG. 1.

In an example, the proximal portions 103A-B can be intercoupled to each other, such as at a pivot or other moving or flexing joint 110. The joint 110 can be configured to hold the proximal portions 103A-B close to each other while permitting the distal portions 105A-B to be movably spread apart from each other. This can allow measuring of an amount of cervical dilation, such as when the distal portions 105A-B are positioned within or beyond the cervical opening, for example, such that the distance between at least one of the distal portions 105A-B, the intermediate portions 104A-B, or the proximal portions 103A-B represents the amount of cervical dilation. In an example, the cervical dilation meter 100 can include a cervical dilation gauge assembly 112, which can include a stem 114. The stem 114 can have a length (e.g., such as about 33 centimeters) that extends from its distal portion, such as at the joint 110, to its proximal portion, which can include or be coupled to an external gauge. The external gauge can be configured to provide a user with a visual or other external indication of the amount of cervical dilation. This external indication can be based upon cervical dilation information that is communicated along the stem 114, such as explained below.

In an example, the spreading apart of the distal portions 105A-B of the arms 102A-B results from providing a bias force that is communicated to the distal portions 105A-B of the arms 102A-B In an example, the cervical dilation meter 100 can be configured such that the bias force against the cervical or vaginal walls is enough to hold the cervical dilation meter 100 apparatus in place, with the distal portions 105A-B in or beyond the cervical opening, such as to allow measuring of the amount of cervical dilation, but not such much as to significantly distort the dilation measurement. In an example, the cervical dilation meter 100 apparatus is held in place using the bias force and without requiring active fixation of such distal portions 105A-B to the cervix. This means that attachment to the cervix by clipping to tissue or by penetrating tissue is not required. By not requiring active fixation, the present techniques can increase convenience and can reduce discomfort, tissue trauma, or risk of infection. Instead of using active fixation, the present techniques can provide an outward lateral force can cause the arms 102A-B to be continuously engaged with vaginal walls or cervical walls. The lateral outward force is sufficient to overcome the inward lateral force exerted by the vaginal and cervical walls against the arms 102A-B. Engagement of proximal portions of the arms 102A-B with the vaginal walls, e.g., because of their shape, allows the internal portions of the cervical dilation meter 100 to be secured and retained within the body cavity, while engagement of the distal ends of the arms 102A-B with the cervical walls allows the relative movement of the arms 102A-B to measure cervical dilation without requiring the active fixation of invasive physical penetration, or attachment or gripping of cervical tissue (e.g., by needles, barbs, clamps, clips, grips).

In an example, the bias force can be provided at least in part by a spring 118, such as can be located about a pin of a rotational pivot joint 110, or located elsewhere. In an illustrative example, the spring 118 can have about six coils, an inner diameter of about 0.454 inches, an outer diameter of about 0.556 inches, a body length of about 0.39 inches, a wire diameter of about 0.051 inches, and can be wound around a mandrel having a mandrel diameter of about 0.36 inches, such available from Century Spring Corp. of Los Angeles, Calif., U.S.A. or Lee Spring Co. Other spring dimensions or configurations can be used, for example, such as can have between 5.0 and 8.0 coils, an inner diameter between about 0.2 inches and about 0.4 inches, an outer diameter between about 0.25 and 0.55 inches, a body length of about 0.18 and 0.4 inches, or other suitable dimensions or configurations.

However, neither a rotational pivot joint, or a spring is required. In an example, the bias force can be provided at least in part by a shape-memory property of the plastic or other material used for the arms 102A-B, such as in an example in which the proximal ends of the arms 102A-B can instead be joined together by a flexing joint 110, such as in a manner like that of a tweezers or forceps. In another example, the bias force can be provide at least in part by a spring 122, such as can be located along the stem 114, such as at or near its proximal portion, or at or near its distal portion. In an illustrative example, the bias force can be communicated from a spring 122 at or near the proximal end of portion stem 114 to the arms 102A-B, such as via an elongate member extending along the stem 114. In an example, such an elongate member can include a cable or a rack (e.g., of a rack-and-pinion) or a shaft, such as explained below.

Figure 2:
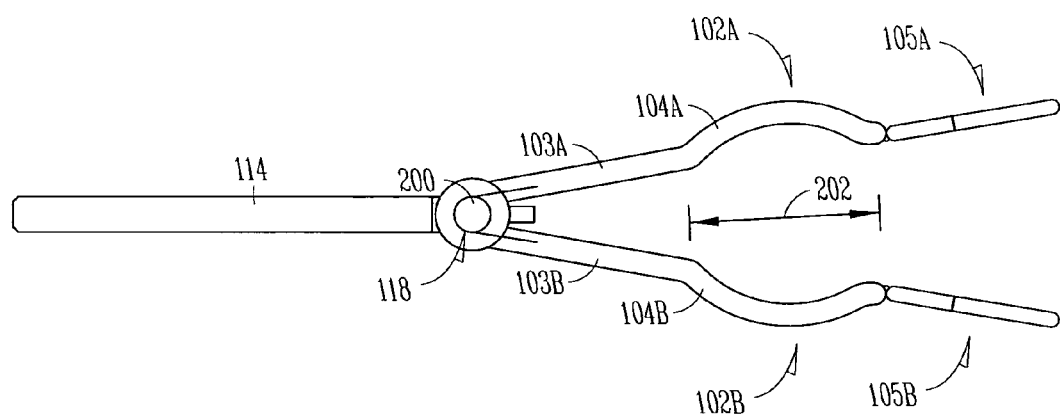
FIG. 2 illustrates a top view of an example of portions of the cervical dilation meter, the arms of which can be drawn together into a closed position for insertion.

FIG. 2 illustrates a top view of an example of portions of the cervical dilation meter 100, the arms 120A-B of which can be drawn together into a closed position for insertion. As illustrated in the example of FIG. 2, the bias force can be provided at least in part by the spring 118, such as can be located about the pin 200, such as with spring ends inserted into and retained by the respective arms 102A-B. As can be observed by viewing the example of FIG. 2, the bias force holding the apparatus in place need not be confined to the distal portions 105A-B of the arms 102A-B pressing against the internal walls of the cervix. In the example of FIGS. 1-2, the intermediate portions of the arms 102A-B can include outwardly bowed intermediate portions 104A-B. These outward bows can be referred to as cephalic curves. In an example, the outward-facing convex sides of the outwardly bowed intermediate portions 104A-B are shaped so that they can engage the respective opposing vaginal walls or proximal outer regions of the cervix, when inserted. This can help deliver a portion of the bias force to the respective vaginal walls or proximal outer regions of the cervix, which can help hold the cervical dilation meter 100 in place, such as while measuring the change in cervical dilation from zero (0) centimeters to ten (10) centimeters during early labor. In an example, the bowed cephalic curves of the intermediate portions 104A-B can be sized and shaped to accommodate a descending fetal head between their opposing concave portions during birthing. In an example, the fetal head can be accommodated within the cephalic curves without dislodging the cervical dilation meter 100, such as until the descending fetal head begins to push against the concave portions of the cephalic curves, which can then automatically dislodge the cervical dilation meter 100 without requiring any clinician or other user intervention. In another example, entry of the fetal head between the opposing concave portions of the cephalic curves during birthing automatically dislodges the cervical dilation meter 100, without requiring any clinician or other user intervention.

In an example, the cephalic curves can respectively include a chordal length 202 (directly across) of about 3.5 cm. In an example, the cephalic curves can respectively include a curved or circumferential length of about 4.75 cm. In an example, the cephalic curves are bowed out by an amount that is between about 0.5 cm and about 1.0 cm from the chordal dimension.

Figure 3:
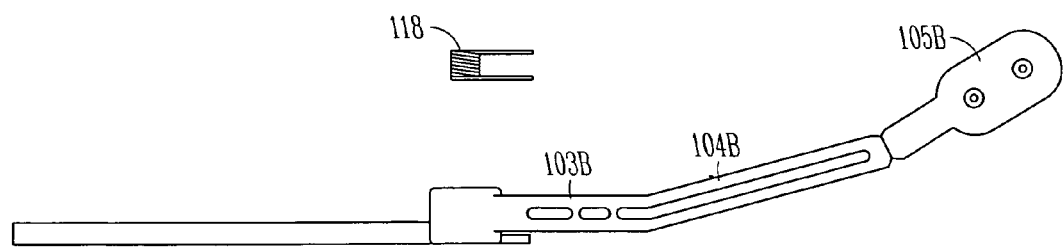
FIG. 3 illustrates a side view of an example of portions of the cervical dilation meter.

FIG. 3 illustrates a side view of an example of portions of the cervical dilation meter 100. In an example, the intermediate portions 104A-B of the respective arms 102A-B can respectively extend upward from a plane formed by the proximal portions 103A-B of the respective arms 102A-B, such as by an angle of about 15 degrees. This upward angle or curvature (which can be referred to as a pelvic curve) can help allow placement of the cervical dilation meter 100 even if the cervix is in a mid or anterior position.

In an example, the respective distal portions 105A-B of the respective arms 102A-B can extend upward from a plane formed by the intermediate portions 104A-B of the respective arms 102A-B, such as by an angle that is about 30 degrees. This upward angle can help allow the cervical dilation meter 100 to be placed such that the respective distal portions 105A-B of the respective arms 102A-B can be easily positioned in the cervical canal, just above the internal cervical os, below the fetal head.

Figure 4:
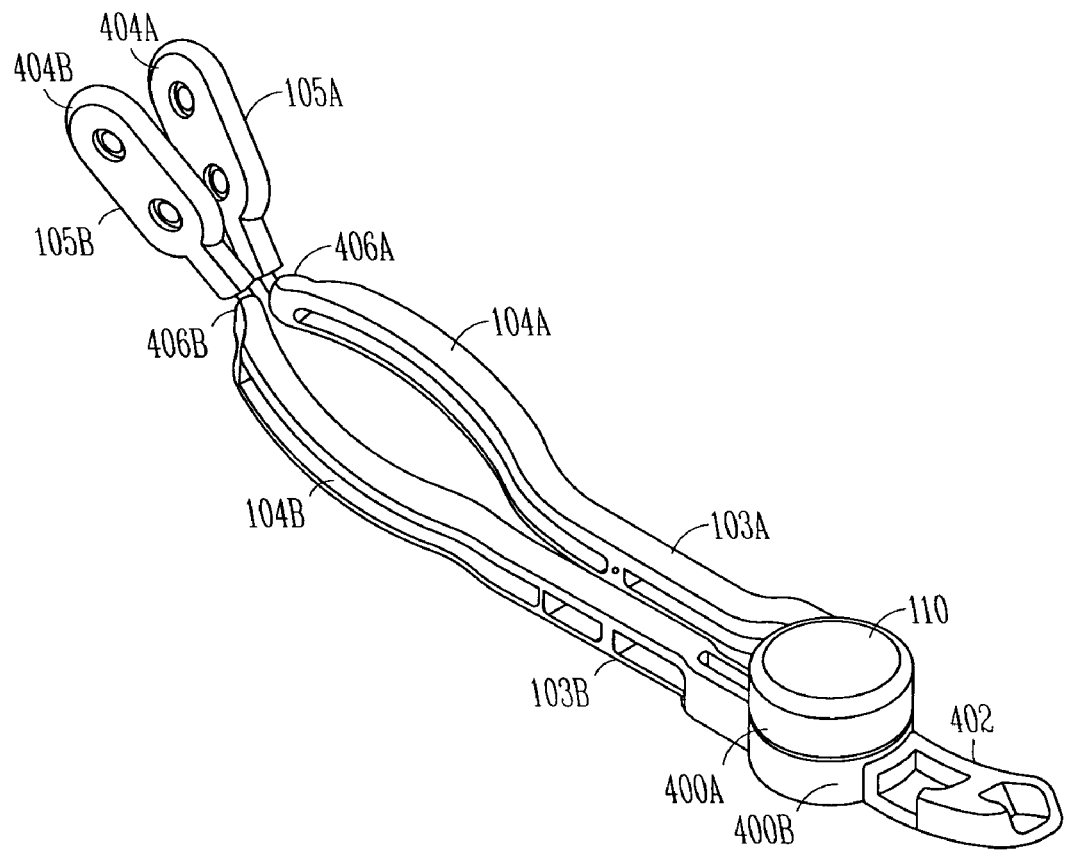
FIG. 4 illustrates an isometric view of an example of the arms, including an example of the pivot joint.
Figure 5:
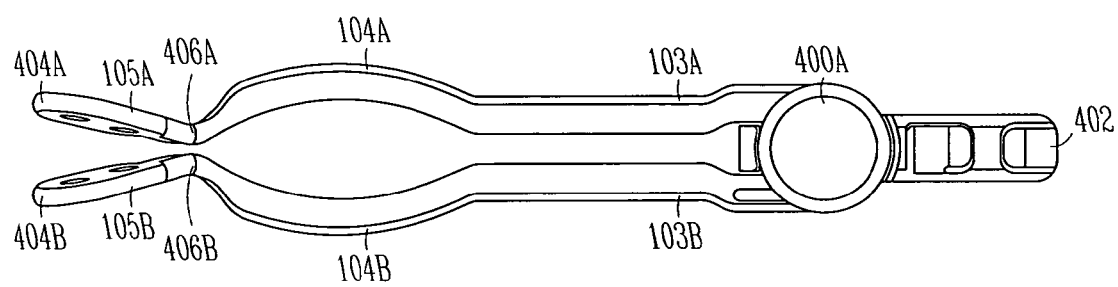
FIG. 5 illustrates a top view of the example of the arms, including an example of the pivot joint.
Figure 6:
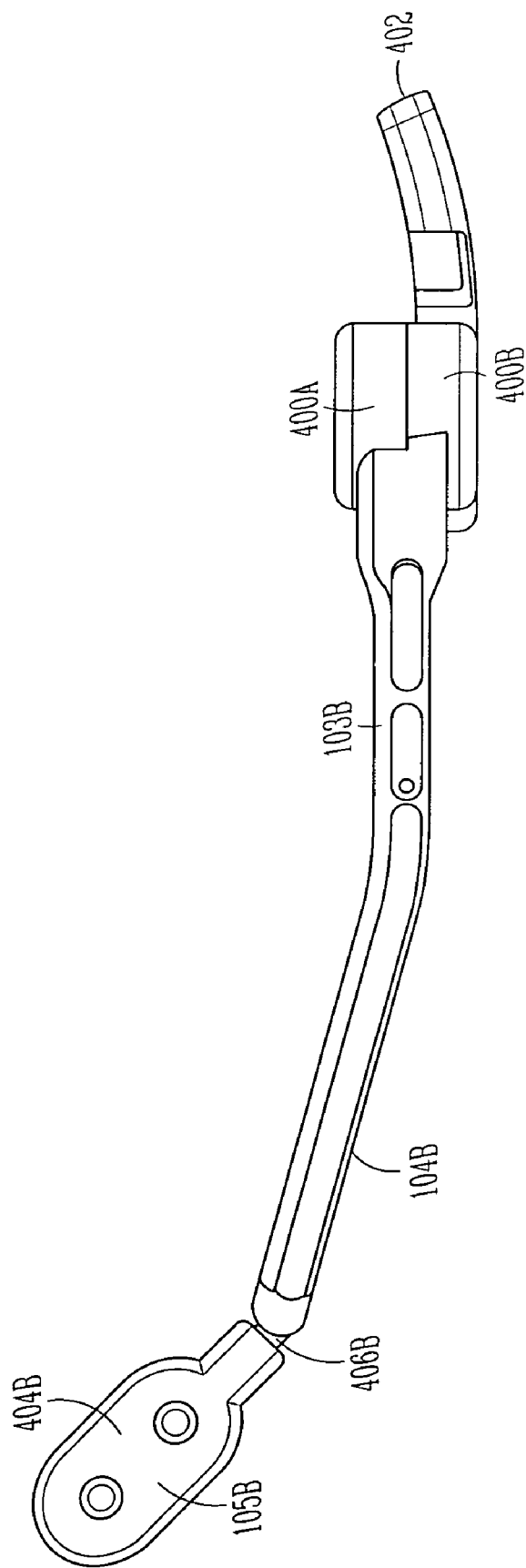
FIG. 6 illustrates a side view of the example of the arms, including an example of the pivot joint.
Figure 7:
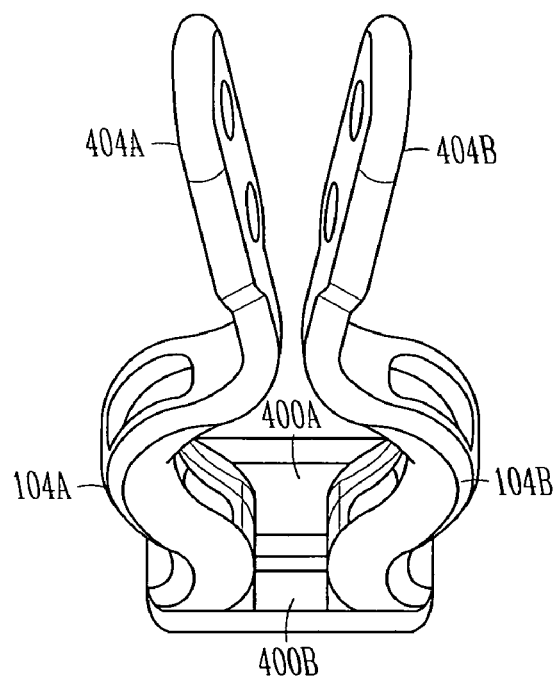
FIG. 7 illustrates a front view of the example of the arms, including an example of the pivot joint.
Figure 8:
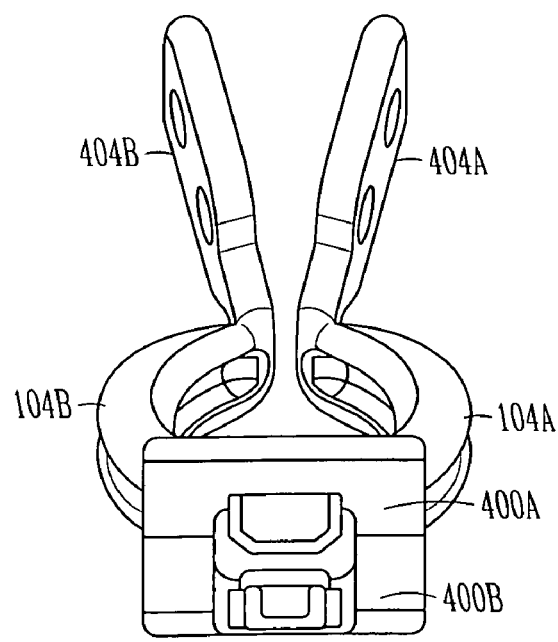
FIG. 8 illustrates a front view of the example of the arms, including an example of the pivot joint.

FIG. 4 illustrates an isometric view, FIG. 5 illustrates a top view, FIG. 6 illustrates a side view, FIG. 7 illustrates a front view, and FIG. 8 illustrates a back view of an example of the arms 102A-B, including an example of the pivot joint 110, in which facing opposing-shell pivot joint housings 400A-B can be used to carry the spring 118 and the pin 200. In this example, one of the housings 400A-B can be coupled to a snap-in receptacle 402, which can extend outward from the housing 400B, such as at an angle of about 20 degrees. A distal portion of the stem 114 can be inserted into and retained by the receptacle 402, such as by snap-fitting the stem 114 into the angled receptacle 402. In an example, the angled receptacle 402 can permit the inserted stem 114 to bend slightly toward the same side of the apparatus 100 as the intermediate portions 104A-B and the distal portions 105A-B.

In an example, the respective distal portions 105A-B can include substantially flat or other feet 404A-B. In an example, each foot 404A-B can provide an outward-facing surface area that can be between about 2.4 cm$^2$ and about 3.84 cm$^2$. The feet 404A-B can have rounded or otherwise atraumatic distal corners and edges, or can be made of (or coated by) a softer durometer material, such as to help avoid or reduce the possibility of tissue abrasion or other injury to the mother or fetus. In an example, the feet 404A-B can be hingedly or flexibly attached to the intermediate portions 104A-B, such as by respective flexing couplers 406A-B. In an example, the flexing couplers 406A-B can include portions that are thinner than the respective feet 404A-B and thinner than the respective intermediate portions 104A-B, such as to provide the flexing. The flexing between the feet 404A-B and the respective intermediate portions 104A-B can, in an example, help resist upward movement of the cervical dilation meter 100 into a lower uterine segment. Such flexing can also help accommodate downward pressing of the fetal head against the feet 128A-B in an example. Such flexing can also help ease removal of the cervical dilation meter 100 without damaging cervical, vaginal, or other tissue during the removal. In an example, the inward facing portions of one or both of the feet 404A-B can optionally include a pressure sensor, such as to monitor pressure of the fetal head pressing against such inward-facing portions of the feet 128A-B. Moreover, the orientation of the flexing feet 404A-B, in combination with the cephalic curves of the intermediate portions 104A-B of the arms 102A-B can help direct pressure, delivered outward by the feet 404A-B, more laterally against the cervical walls, rather than directing such pressure upward toward the uterus.

Figure 9:
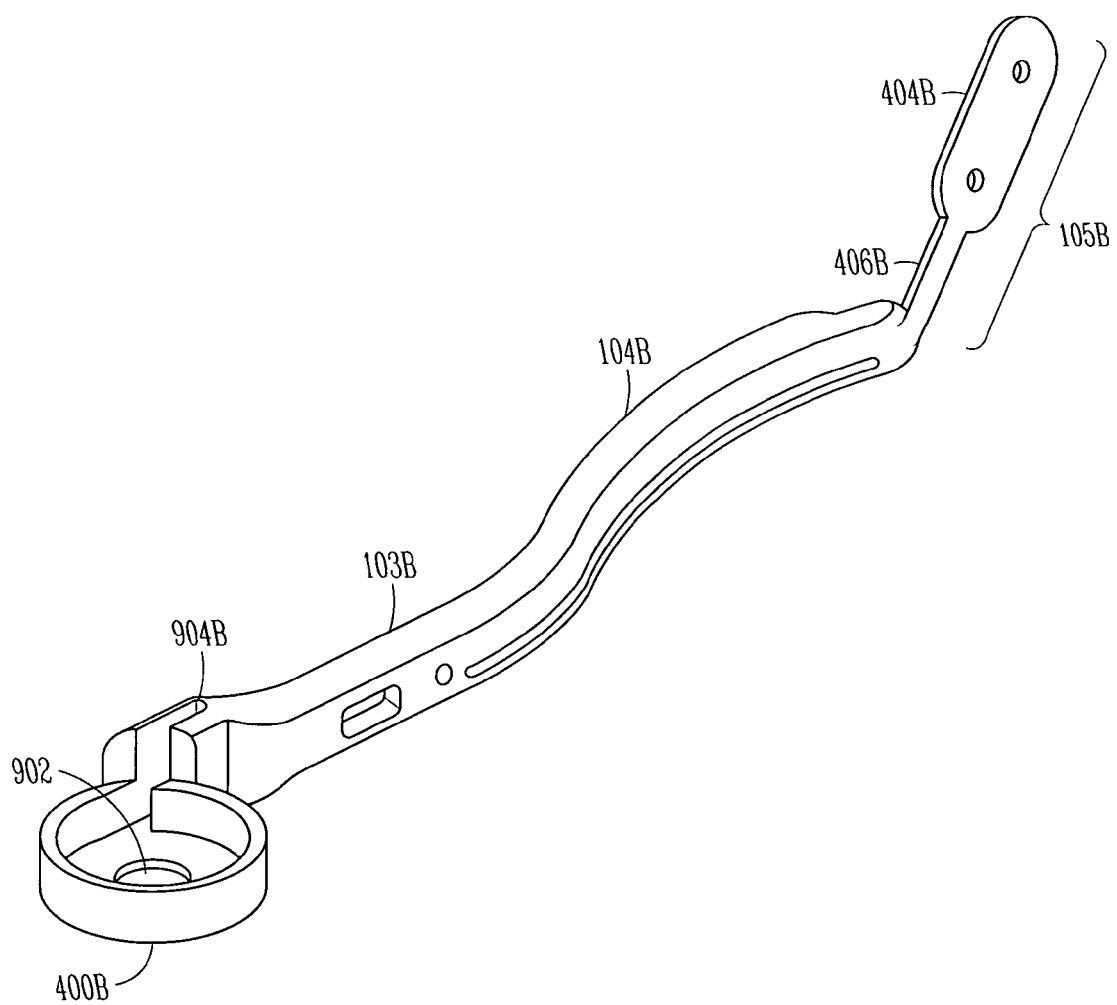
FIG. 9 illustrates an isometric view of an example of an arm and, at its proximal portion, a pivot joint.

FIG. 9 illustrates an isometric view of an example of an arm 102B and, at its proximal portion, a pivot joint 110 including a pivot joint housing 400B including an opening 902 into which the pin 200 (of the opposing pivot joint housing 400A at a proximal portion of an arm 102A) can be inserted. This allows rotational pivoting about the pin 200, which can be driven by the spring 118 carried within the housings 400A-B, with ends of the spring 118 received into respective slots 904A-B in the respective arms 102A-B. In this way, the spring 118 can press against the outward sidewalls of the slots 904A-B to impart the outward bias force to the arms 102A-B, such as to hold the apparatus 100 in place for measuring cervical dilation.

In examples such as those shown in FIGS. 1-9, portions of the apparatus 100, such as the arms 102A-B, the pivot joint 110, the stem 114, or other portions, can include or consist of molded polypropylene. This can provide an inexpensive apparatus 100, such as to provide a single-use disposable apparatus 100. In another example, brass or aluminum components can be used, such as to provide a more durable re-usable apparatus 100 that can be heat or chemically sterilized between uses.

Figure 10:
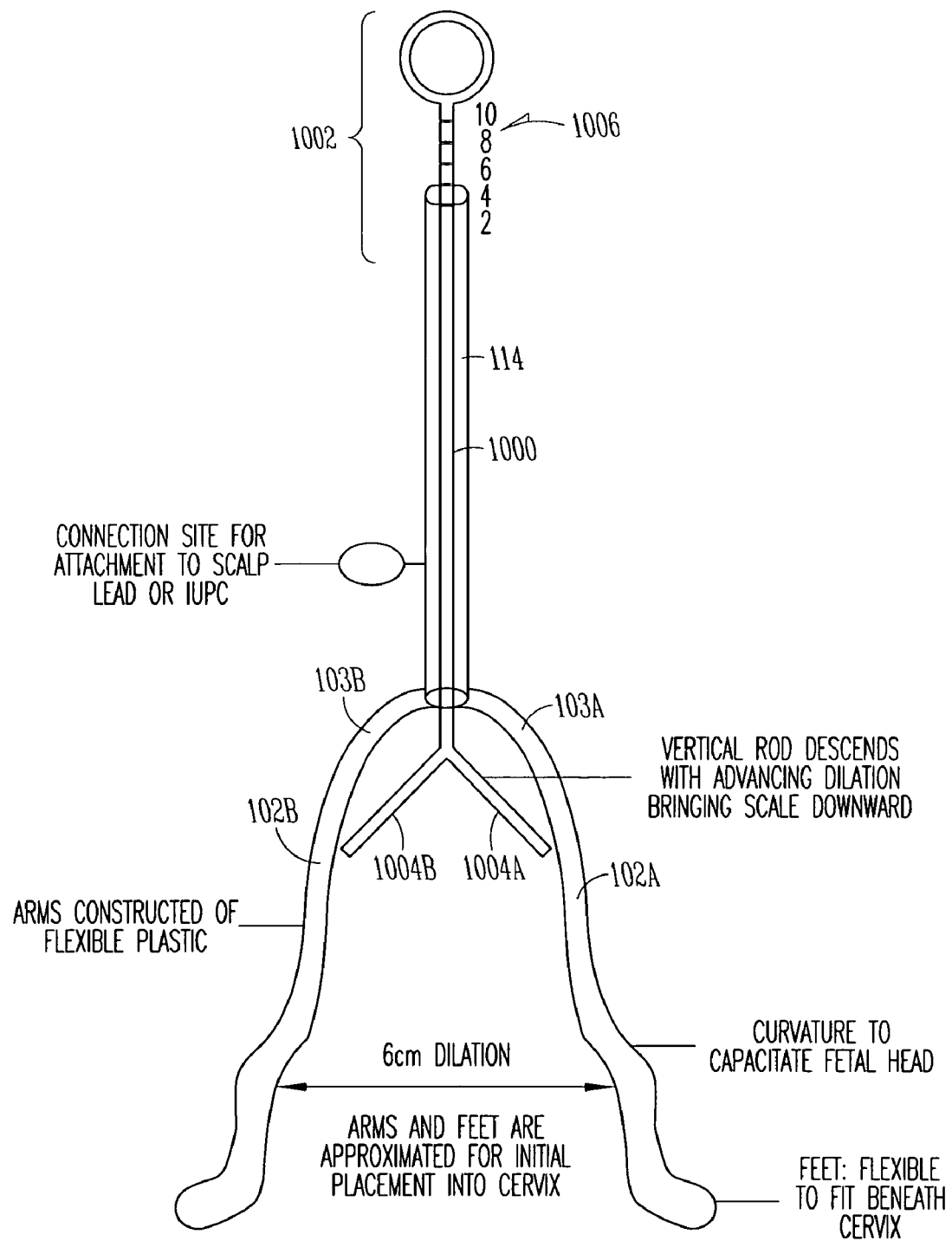
FIG. 10 is a schematic illustration of an example of a dilation meter, in which the stem can be hollow or otherwise configured to guide a rod that extends longitudinally along a length of the stem.

FIG. 10 is a schematic illustration of an example of a dilation meter 100, in which the stem 114 can be hollow or otherwise configured to guide a rod 1000 or other member that extends longitudinally along a length of the stem 114. This can permit communicating of cervical dilation information from the arms 102A-B to an external gauge 1002. The example of FIG. 10 illustrates that a rotational pivot joint 110 can be omitted. Instead, the arms 102A-B can be joined (e.g., in a wishbone-like fashion) to the distal portion of the stem 114. A shape memory property of the arms 102A-B and their respective attachments to the stem 114 can allow the distal portions of the arms 102A-B to be drawn together, such as for insertion into the cervix, and to be self-spread apart, such as during the cervical dilation, such as to provide information about the degree of the cervical dilation.

In the example of FIG. 10, a distal portion of the rod 1000 can be pivotably connected (e.g., via a pin) to proximal portions of respective resilient linkages 1004A-B. The distal portion of the linkage 1004A can be pivotably connected to the arm 102A, such as via a pin at a proximal portion 103A (as shown) or to a more distal portion of the arm 102A. The distal portion of the linkage 1004B can be similarly pivotably connected to the arm 102B, such as via a pin at a proximal portion 103B (as shown) or to a more distal portion of the arm 102B.

In this way, as the arms 102A-B spread apart from each other, a proximal portion of the rod 1000 is drawn into a proximal portion of the tubular or other stem 114 and, concurrently, a distal portion of the rod 1000 is extended out from a distal portion of the tubular or other stem 114.

In an example, the external gauge 1002 can include cervical dilation markings 1006 on the rod 1000, which can be read against the end of the tubular or other stem 114 to provide an external indication of the degree of cervical dilation to a viewing user. For example, the rod 1000 can be manufactured such that the markings 1006 provide a scale that corresponds to the number of centimeters of cervical dilation measured using the arms 102A-B. The scale can be linear, but need not be linear. In an example, there can be a logarithmic correlation between the scale of the markings 1006 on the rod 1000 and the degree of separation of the arms 102A-B, which provides the indication of cervical dilation.

Figure 11:
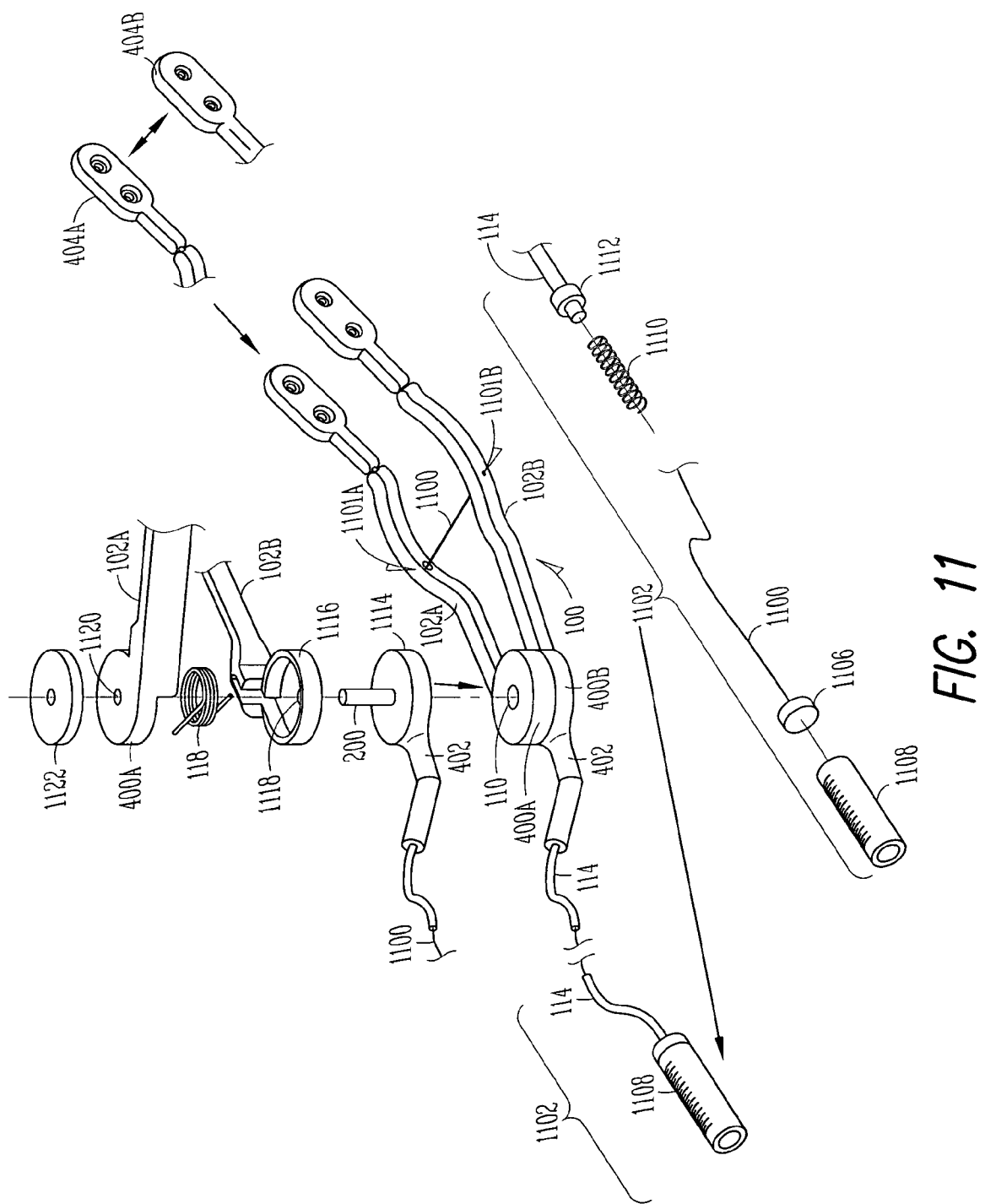
FIG. 11 is an exploded view of an example of portions of the apparatus in which a flexible string or cable can be used (e.g., instead of the rod) to communicate the cervical dilation information from the arms to an external gauge.

FIG. 11 is an exploded view of an example of portions of the apparatus 100 in which a flexible string or cable 1100 can be used (e.g., instead of the rod 1000) to communicate the cervical dilation information from the arms 102A-B to an external gauge 1102. A distal end of the cable 1100 can be anchored or otherwise affixed at one of the arms 102A-B, such as at a proximal portion 103A-B or an intermediate portion 104A-B of the one of the arms 102A-B. Measurement of the indication of cervical dilation at a location that is near the proximal portions 103A-B of the arms can help avoid entanglement or obstruction of the cable 1100 by the fetal head or other instrumentation that may be inserted into a vagina, cervix or uterus. In an example, the cable anchoring or affixing can involve tying off or otherwise widening a distal end of the cable 1100 and inserting the cable 1100 through a hole 1101B in the one of the arms 102A-B, such that the widened end of the cable 1100 cannot be pulled through the hole 1101B in the one of the arms 102A-B. The cable 1100 can then extend across to the other one of the arms 102A-B, such as through an opposing hole 1101A in the other one of the arms 102A-B. The cable 1100 can then extend within or along a tubular lumen, sheath, or other cable guide along that other one of the arms 102A-B, into or along the pivot joint housing 400A-B, within or along the receptacle 402, within or along the stem 114, and to the external gauge assembly 1102.

At the external gauge assembly 1102, the cable 1100 can terminate at a gauge plunger 1106, which can travel back-and-forth within a transparent cylindrical or other elongate gauge body 1108, as the arms 102A-B are drawn toward each other or spread apart from each other. Scale markings on the gauge body 1108 can be read against the gauge plunger 1106 to provide an external indication of cervical dilation. Tension in the cable 1100 can be maintained by a compression spring 1110, which can be located around the cable 1100, such as at or near the proximal end of the cable 1100. The compression spring 1110 can be used in addition to the spring 118, in an example, or instead of the spring 118, in another example. The cable-tensioning compression spring 1110 can have its proximal end seated against the plunger 1106 and its distal end seated against a stop 1112 portion of the stem 114. In an example, a distal portion of the gauge body 1108 can also be seated against the stop 1112. In an example (not shown in FIG. 11), the compression spring 1110 can instead be located near the pivot 110, for example, its force can be communicated to the external gauge assembly by a rod or tube within the stem 114.

The exploded view example of FIG. 11 also demonstrates an example in which the pivot 110 can include a disk-like base portion 1114, coupled to the receptacle 402, and including the pin 200. The pivot 110 can also include a proximal end of the arm 102B, which can include a housing 400B that includes disk 1118 having a center hole 1116 through which the pin 200 can be inserted. Next, the spring 118 can then be placed about the pin 200, such as with one end of the spring 118 inserted into or otherwise constrained by the arm 102B, and the other end of the spring 118 then inserted into or otherwise constrained by the arm 102A. Next, the proximal end of the arm 102A, which can include a cylindrical housing to carry the spring 118 and a center hole 1120, can be placed with the center hole 1120 about the pin 200, with the end of the spring 118 constrained by the arm 102A, such as explained above. Then, a snap-on cap 1122 can be placed about and snapped onto the pin 200, which can help hold the various components of the pivot 110 together.

Figure 12:
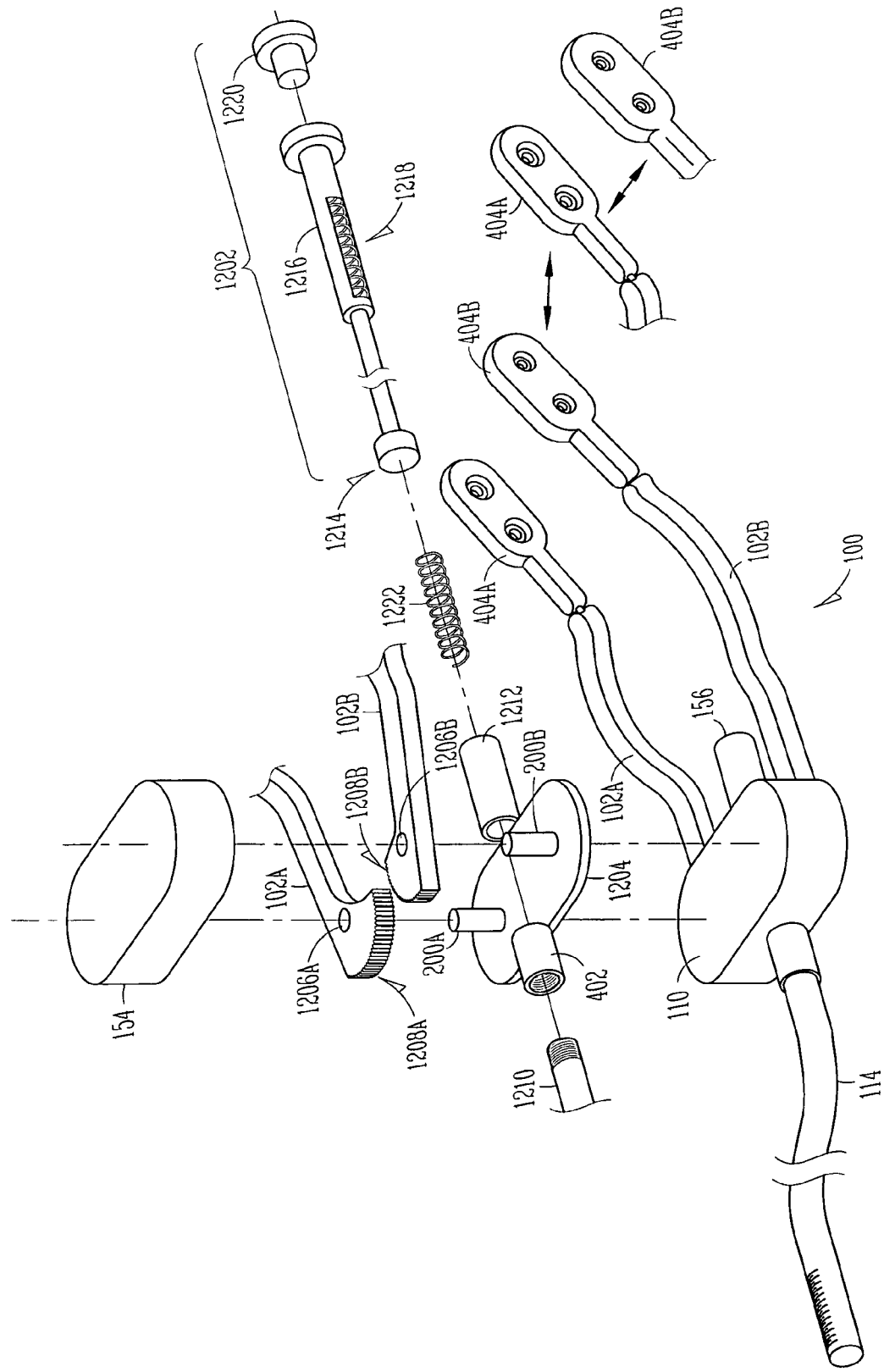
FIG. 12 is an exploded view of an example of portions of the apparatus in which a rack-and-pinion configuration of the pivot can be used (e.g., instead of a rod or a flexible string or cable) to communicate the cervical dilation information from the arms to an external gauge assembly.

FIG. 12 is an exploded view of an example of portions of the apparatus 100 in which a rack-and-pinion configuration of the pivot 110 can be used (e.g., instead of a rod 1000 or a flexible string or cable 1100) to communicate the cervical dilation information from the arms 102A-B to an external gauge assembly 1202. In this example, the pivot 110 can include a pinion pivot base 1204. The stem receptacle 402 can extend outward from the pivot base 1204, in a similar manner to that described above. The base 1204 can include separate pins 200A-B that can extend upward into respective receptacles 1206A-B of respective arms 102A-B. This can allow the respective arms 102A-B to pivot about their respective pins 200A-B. This can allow the arms 102A-B to be drawn toward each other or spread apart from each other. The pivoting proximal ends of the arms 102A-B can include opposing facing pinion toothed gears 1208A-B. A toothed geared distal portion of a rack 1210 can be inserted between the opposing facing pinion toothed gears 1208A-B. Like the rod 1000, the rack 1210 can extend proximally through the tubular stem 114 to an external gauge assembly 1202. In an example, a distal portion of the rack 1210 can travel into a rack receptacle 1212. A proximal end of the rack 1210 can include a plunger 1214 that travels within an at least partially transparent barrel 1216. The barrel can include markings 1218 forming a cervical dilation scale for user readout. In this way, as the cervix dilates, and the distal portions of the arms 102A-B spread apart, a distal end of the rack 1210 travels toward or into the receptacle 1212, and a proximal end of the rack 1210 travels such that the rack plunger 1214 moves more distally within the barrel 1216 of the dilation gauge assembly 1202. The barrel 1216 can include an end-cap 1220 at its proximal end. A spring 1222 can be located near the proximal or distal portion of the rack 1210, such as at the barrel 1216 or at the receptacle 1212. The spring 1222 can be used to bias the rack 1210 in a distal direction such that the arms 102A-B tend to self-spread apart, such as to allow measurement of the cervical dilation. The spring 1222 can be designed to provide a pushing or pulling force, as appropriate, to provide such a bias force to tend to spread the arms 102A-B apart. A cap 1224 can be snap-fitted onto the pins 200A-B, such as to hold or house the components of the rack-and-pinion pivot 110.

In an example, the apparatus 100 can be packaged together in a kit with an introducer that can hold the arms 102A-B together during insertion. In an example, the introducer can include a peel-away sheath that keeps the arms 102A-B together during insertion, but which can include two separate proximal tails that can be used to concurrently pull apart and retract the sheath, leaving the arms 102A-B in place in the opening of the cervix, and thereby permitting such arms 102A-B to self-expand apart from each other to measure the cervical dilation. In another example, the apparatus 100 can be provided with a proximal push-rod such as to communicate a force to hold the arms 102A-B together during insertion.

Figure 13:
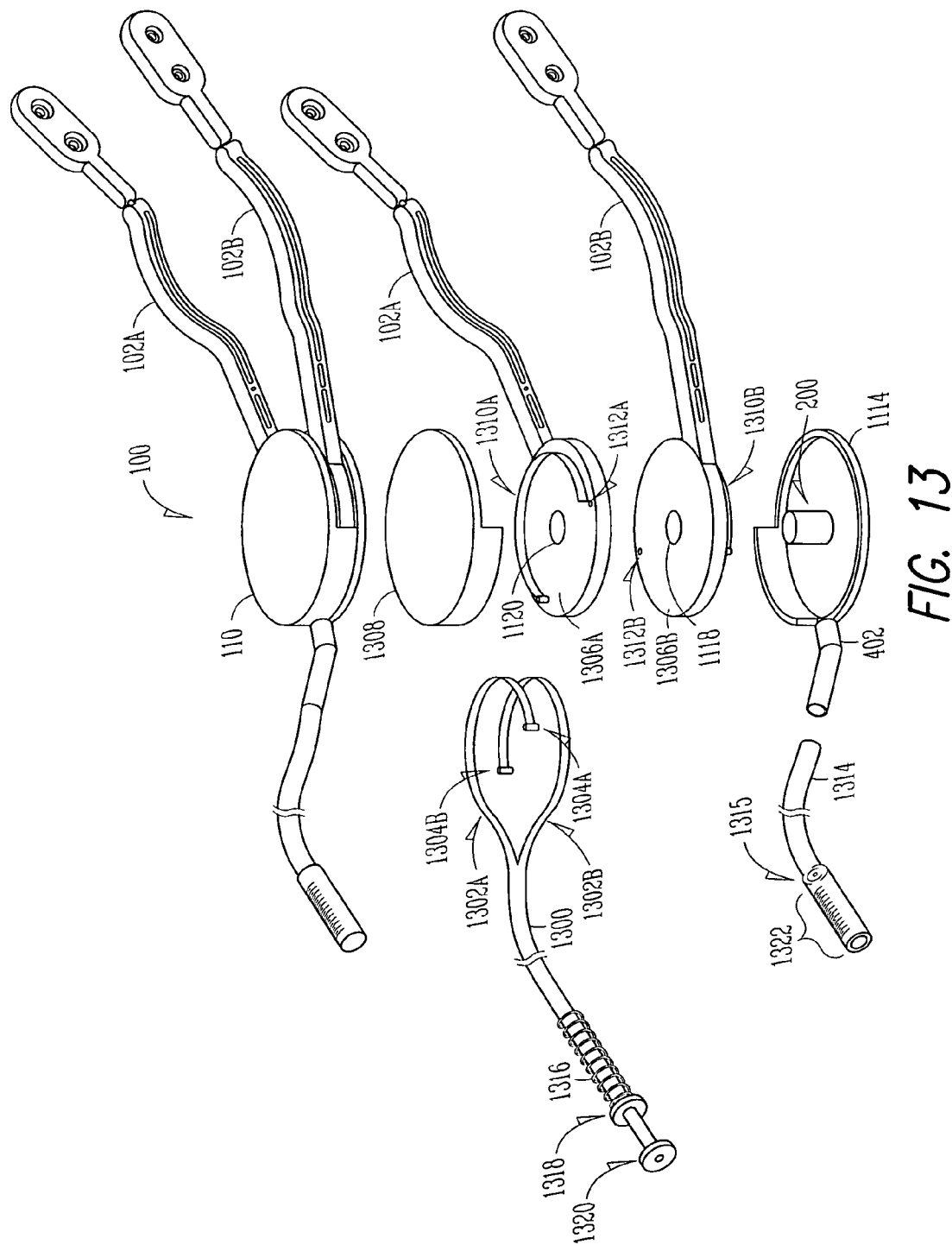
FIG. 13 is an exploded view of an example of portions of the apparatus in which a tension cable can be used to communicate a force, such as to bias the arms away from each other.

FIG. 13 is an exploded view of an example of portions of the apparatus 100 in which a tension cable 1300 can be used to communicate a force, such as to bias the arms 102A-B away from each other. In an example, the tension cable 1300 can include a bifurcated distal portion 1302A-B. The distal portion 1302A can terminate at a coupling feature such as a post 1304A, which can extend perpendicular to the distal portion 1302A. The distal portion 1302B can terminate at a coupling feature such as a post 1304B, which can extend perpendicular to the distal portion 1302B.

In the example of FIG. 13, proximal ends of the arms 102A-B can be coupled together, such as at a pivot joint 110, which can include respective disks 1306A-B at the respective proximal ends of the arms 102A-B. The disks 1306A-B can include respective center holes 1120, 1118 through which a pin 200 can be inserted. A distal end of the pin 200 can be snap fitted into or otherwise engaged to a cap 1308, thereby holding together the cap 1308, the disks 1306A-B, the pin 200 and the disk 1114, such as to provide the joint 110.

In the example of FIG. 13, the disks 1306A-B can include arc-shaped, semicircular, or similar guide rails 1310A-B. The cable distal portions 1302A-B can respectively wrap around the outsides of the respective rails 1310A-B. The posts 1304A-B can be respectively inserted into and engage the respective recesses 1312A-B. The cable 1300 can pass through a tubular receptacle 402 and a flexible tubular or other sheath 1314 back to a proximal gauge 1316, which can be located external to the patient when the distal portions of the arms 102A-B are located within the cervix, such as to measure its diameter.

In an example, the gauge 1316 can include a proximal end of the sheath 1314, which can include an outward flange 1315, which can serve as a distal stop for a spring 1316. An outward flange 1318 near a proximal end of the cable 1300 can serve as a proximal stop for the spring 1316. In such an example, the spring 1315 can be captured between the flanges 1315 and 1318. In an example, the spring 1315 can provide the force that is communicated by the cable 1300 to the arms 102A-B such as to bias the arms 102A-B away from each other during the cervical dilation measurement. In an example, a gauge pointer 1320 is optionally coupled to the flange 1318 at the proximal end of the cable 1300, such as for reading the cervical dilation against graduations or demarcations on a transparent or translucent gauge cylinder 1322. In another example, the flange 1318 can itself optionally be used to provide a gauge pointer for reading against the graduations or demarcations on the gauge cylinder 1322. In another example, the apparatus 100 can be provided with a proximal push-rod (e.g., extending further proximally from the gauge pointer 1320) such as to communicate a force to hold the arms 102A-B together during insertion. A dial or other gauge readout can be substituted for the linear translational gauge cylinder in this example or in one or more of the other examples described herein.

Figure 14:
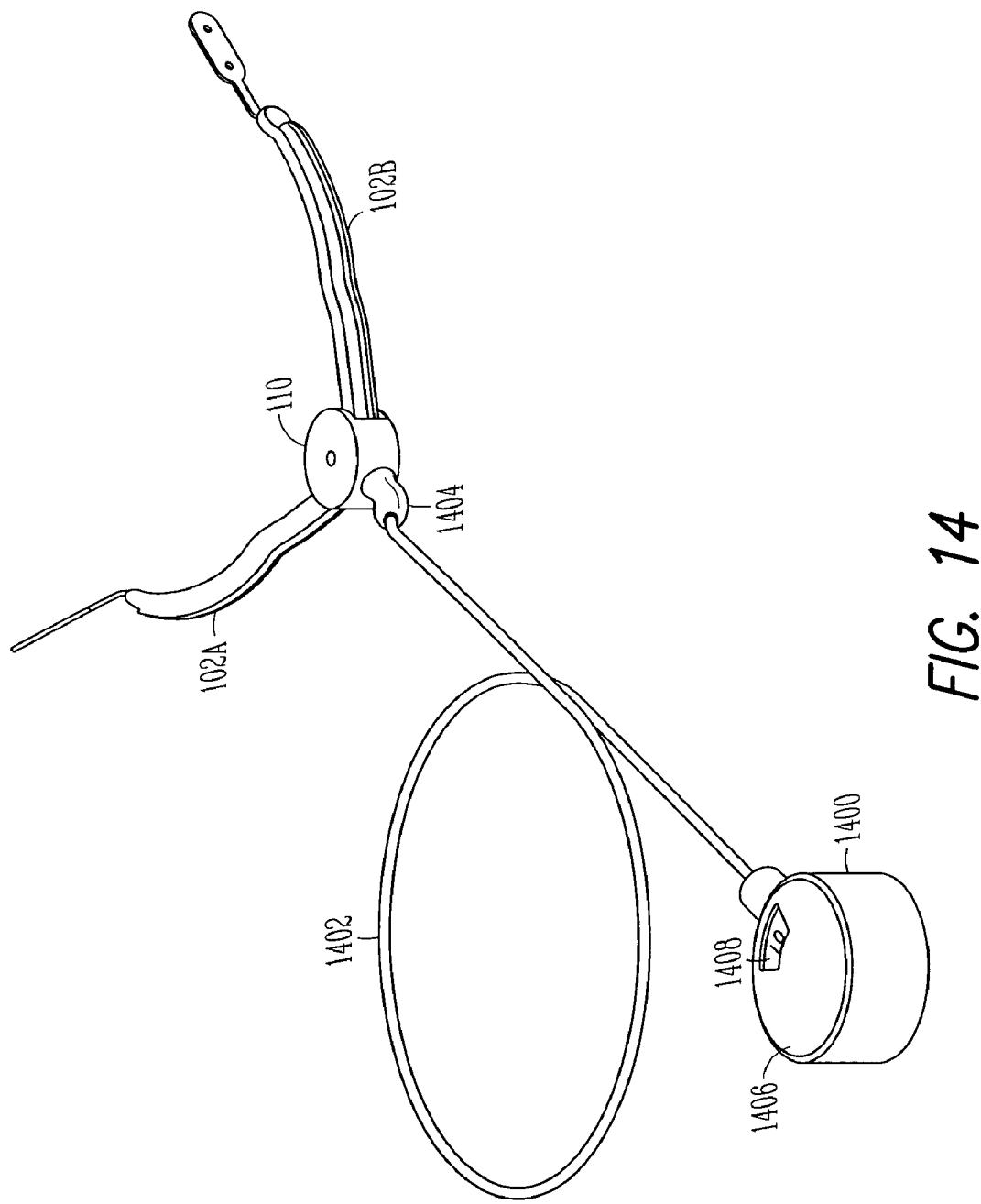
FIG. 14 is an example of portions of the apparatus in which a dial gauge can be provided and coupled via a cable within a flexible sheath to a receptacle of a pivot joint from which the arms extend.

FIG. 14 is an example of portions of the apparatus 100 in which a dial gauge 1400 can be provided and coupled via a cable within a flexible sheath to a receptacle 1404 of a pivot joint 110 from which the arms 102A-B extend. The dial gauge 1400 can include a dial gauge housing 1406 having a window 1408 through which a dilation reading on a rotating dial can be read.

Figure 15:
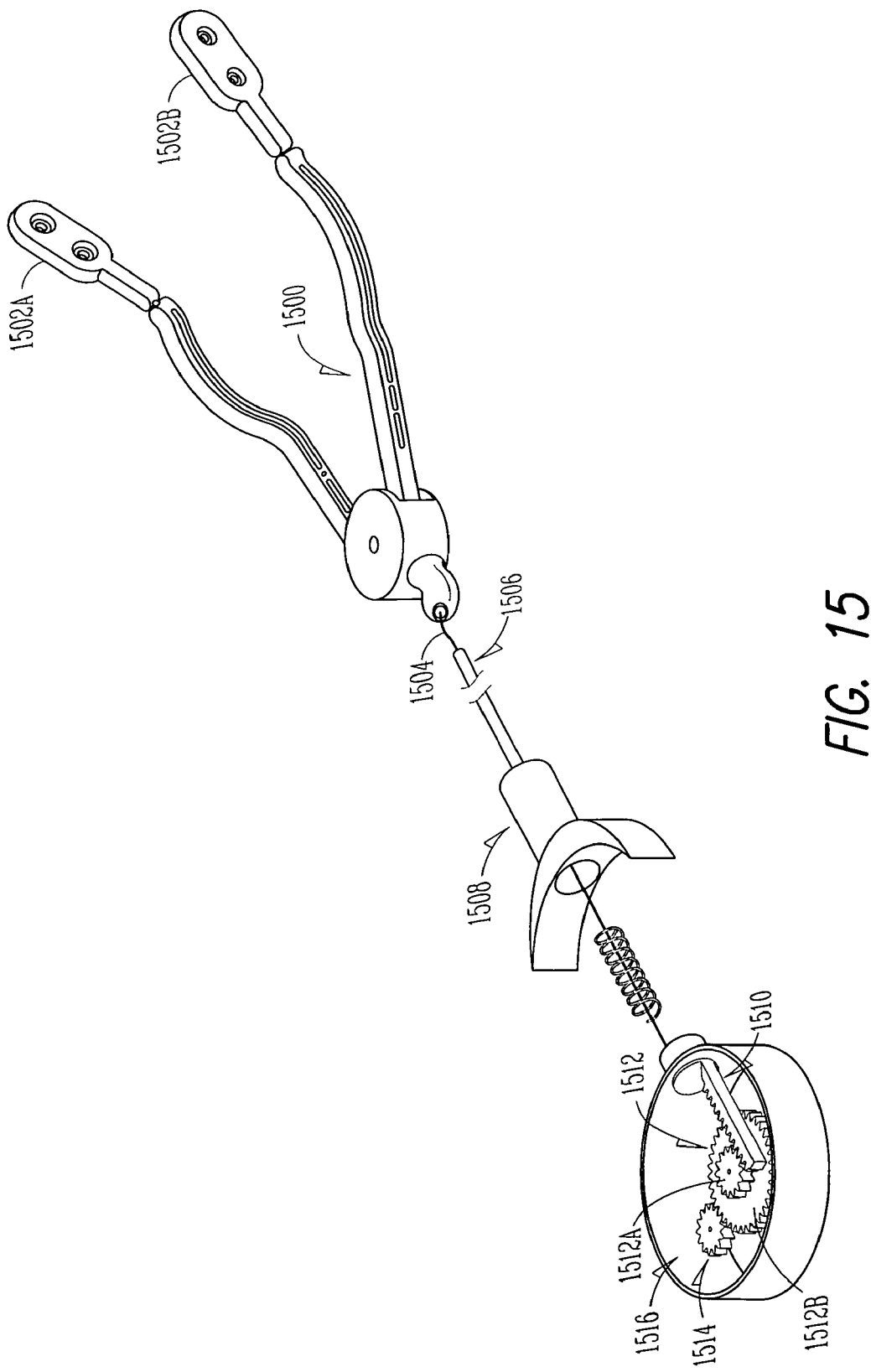
FIG. 15 is a schematic diagram corresponding to an example of the apparatus such as shown in the example of FIG. 14.

FIG. 15 is a schematic diagram corresponding to an example of the apparatus 100 such as shown in the example of FIG. 14. In this example a short cable 1500 can include ends with respective couplers, such as balls 1502A-B, that can be coupled to respective arms 102A-B, such as by being inserted into respective sockets in the respective arms 102A-B at a desired proximal, intermediate, or distal location along the length of such arms 102A-B. A middle region of the cable 1500 can be coupled to a distal end of a longer cable 1504, which can be passed through a flexible tubular or other sheath 1506. In an example, the sheath 1506 can extend from the receptacle 1404 on the pivot joint 110 to a spring housing 1508. In an example, the spring housing 1508 can extend outward from the dial gauge housing 1406. A proximal end of the cable 1504 can be coupled to a distal portion of a rack gear 1510, which can form a rack-and-pinion arrangement with a pinion gear 1512. The pinion gear 1512 can engage a dial gear 1514, which drives a rotational movement of a dial 1516. The dial 1516 can provide numerical or other indicia indicative of cervical dilation, such as can be viewable through the window 1408 on the housing 1406 of the dial gauge 1400. In an example, the pinion gear 1512 can include a multiple stage pinion gear, such as a two-stage pinion gear, such as to translate linear movement of the rack gear 1510 into a desired degree of rotation of the dial 1516. For example, the two-stage pinion gear 1512 can include a smaller gear 1512A, which engages the rack gear 1510, and which rotates together with a larger gear 1512B, which engages the dial gear 1514. In this example, the spring housing 1508 can include a coil spring 1518, which can be located about the cable 1504 and confined within the spring housing 1508 between the spring housing 1508 and the distal portion of the rack gear 1510. The spring 1518 can provide a force against the rack gear 1510. The rack gear 1510 can communicate this force via the cables 1504 and 1502 to the arms 102A-B such as to bias the arms 102A-B away from each other, such as for performing the cervical dilation measurement.

ADDITIONAL NOTES

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown and described. However, the present inventors also contemplate examples in which only those elements shown and described are provided. However, the present inventors also contemplate examples in which only those elements shown or described are provided. Moreover, the present inventors also examples using any combination or permutation of those elements shown or described, either with respect to a particular example, or with respect to other examples shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. An apparatus comprising:
   first and second arms, comprising respective proximal and distal portions and intermediate regions therebetween, the proximal portions of the first and second arms coupled together, the distal portions of the first and second arms configured to be inserted between opposing lateral walls of a cervix or vagina and measure a cervical dilation, and the intermediate region of the first arm comprising an outwardly bowed first cephalic curve and the intermediate region of the second arm comprising an outwardly bowed second cephalic curve opposing the first cephalic curve,
   the first and second arms configured to exert an outward force against the opposing lateral walls in an amount sufficient to hold the apparatus in position while measuring cervical dilation, without requiring physical penetration, attachment, or gripping of the cervix or vagina,
   a concave portion of the first cephalic curve and a concave portion of the second cephalic curve sized and shaped to receive and accommodate a portion of a fetal head therebetween; and
   a cervical dilation indicator assembly, communicatively coupled to the first and second arms to receive information about the cervical dilation, and comprising an external cervical dilation indicator to provide an indication of the cervical dilation to a user.

2. The apparatus of claim 1, wherein the outward force is of an amount that does not substantially affect the cervical dilation measurement.

3. The apparatus of claim 1, wherein the concave portions of the first and second cephalic curves are sized and shaped to receive a portion of a descending fetal head therebetween during birthing while the first and second arms continue to exert the outward force against opposing lateral walls of the cervix or vagina to hold the apparatus in position while measuring cervical dilation, without requiring physical penetration, attachment, or gripping of the cervix or vagina.

4. The apparatus of claim 1, wherein the first and second arms comprise respective first and second pelvic curves at or near a location between the intermediate regions and proximal portions of the respective first and second arms, such that the respective intermediate regions of the respective first and second arms angle or curve upward from a plane formed by the respective proximal portions of the respective first and second arms at an angle of about 15 degrees to allow placement of the apparatus if the cervix is in a mid or anterior position.

5. The apparatus of claim 1, comprising a spring that is coupled to the first and second arms to provide the outward force and to bias the first and second arms away from each other and against opposing lateral walls of the cervix or vagina.

6. The apparatus of claim 5, wherein the spring is configured to exert the outward force in an amount sufficient to bias the first and second arms against opposing lateral walls of the cervix or vagina to hold the apparatus in position while measuring cervical dilation without requiring physical penetration, attachment, or gripping of the cervix or vagina, and without exerting the outward force in an amount so as to substantially affect the cervical dilation measurement.

7. The apparatus of claim 1, wherein the distal portions of the first and second arms respectively comprise first and second feet that are coupled to the intermediate regions of the respective first and second arms by respective first and second flexible members, having greater flexibility than the first and second feet and the intermediate regions of the first and second arms, and wherein the respective first and second feet are configured to flex at one or more angles, with respect to the first and second arms, in a plane formed by the intermediate regions of the first and second arms.

8. The apparatus of claim 7, wherein the first and second feet are respectively angled upward, from the plane formed by the respective intermediate regions of the first and second arms, at an angle of about 30 degrees.

9. The apparatus of claim 7, wherein the first and second feet respectively provide a surface area of at least about 2.0 cm² for contacting the cervix or vagina.

10. The apparatus of claim 1, comprising:
   a rotational pivot joint, coupling the proximal portions of the first and second arms together; and
   a spring, coupled to the first and second arms to exert the outward force to drive the first and second arms apart and against opposing lateral walls of the cervix or vagina.

11. The apparatus of claim 10, wherein the spring is located at a proximal end of a member extending from a location near or distal to the rotational pivot joint to a more proximal external location.

12. The apparatus of claim 11, wherein the spring is located at the external location.

13. The apparatus of claim 10, wherein the member comprises a cable.

14. The apparatus of claim 10, wherein the member comprises a portion of a rack-and-pinion assembly.

15. The apparatus of claim 10, wherein the spring is located at the rotational pivot joint.

16. The apparatus of claim 1, comprising a stem including:
 a proximal portion coupled to the external indicator of cervical dilation; and
 a distal portion coupled to the proximal portion of at least one of the first and second arms.

17. The apparatus of claim 1, comprising an introducer sheath, sized and shaped to constrain the first and second arms toward each other during insertion of the apparatus.

18. The apparatus of claim 1, comprising a cable including a proximal portion coupled to the external indicator of cervical dilation, and a distal portion coupled to at least one of the first and second arms, and wherein the cable is constrained such that a position of a proximal end of the cable is correlative to the cervical dilation.

19. The apparatus of claim 18, comprising a spring, coupled to a proximal end of the cable, the spring configured to tend to move the proximal end of the cable in a proximal direction to exert, via the cable, a force on at least one of the first and second arms to tend to move respective portions of the first and second arms apart.

20. A method comprising:
 inserting first and second arms, including respective intermediate regions having outwardly bowed cephalic curves, of a cervical dilation measuring apparatus into a vagina such that respective distal portions of the first and second arms exert enough of an outward force against opposing lateral walls of a cervix or vagina to hold the apparatus in position while measuring cervical dilation, without requiring physical penetration, attachment, or gripping to the cervix or vagina;
 communicating information about the cervical dilation to an external location;
 providing an external indicator of the cervical dilation to a user, using the information; and
 receiving a portion of a fetal head between concave portions of the first and second cephalic curves.

21. The method of claim 20, comprising receiving the portion of the fetal head between portions of the first and second arms during birthing while the first and second arms continue to exert enough of an outward force against opposing lateral walls of the cervix or vagina to hold the apparatus in position while measuring cervical dilation without requiring physical penetration, attachment, or gripping of the cervix or vagina.

22. The method of claim 20, comprising placing the apparatus when the cervix is in a mid or anterior position such that respective intermediate portions of the respective first and second arms angle or curve upward, from respective proximal portions of the respective first and second arms, at an angle of about 15 degrees.

23. The method of claim 20, comprising exerting the outward force of the first and second arms against opposing lateral walls of the cervix or vagina in an amount sufficient to hold the apparatus in position while measuring cervical dilation without requiring physical penetration, attachment, or gripping of the cervix or vagina, and without exerting so much outward force so as to substantially affect the measuring of the cervical dilation.

24. The method of claim 20, comprising inserting into a cervical os first and second feet at respective distal portions of the first and second arms, such that the first and second feet flex at an angle, with respect to the respective first and second arms, in a plane formed by intermediate portions of the first and second arms.

25. The method of claim 24, comprising inserting into the cervical os the first and second feet at respective distal portions of the first and second arms, such that the first and second feet are angled upward with respect to the plane formed by the intermediate portions of the first and second arms.

26. The method of claim 20, wherein communicating information about the cervical dilation to the external location comprises receiving the information using a longitudinal position translation correlative to a degree of pivoting of intercoupled proximal portions of the first and second arms.

27. The method of claim 26, wherein using a longitudinal position translation correlative to a degree of pivoting of intercoupled proximal portions of the first and second arms comprises using at least one of:
 a position of a rack in a rack-and-pinion; or
 a position of a proximal end of a member, wherein the member is constrained such that the proximal end of the member represents the degree of pivoting.

\* \* \* \* \*